United States Patent [19]

Gintelia et al.

[11] 3,961,900
[45] June 8, 1976

[54] COMBUSTIBLE VAPOR DETECTOR

[75] Inventors: Louis Gintelia, Gillette; Harry Kundrat, New Providence; Anantha K. S. Raman, Gillette, all of N.J.

[73] Assignee: Catalytic Pollution Controls, Inc., Gillette, N.J.

[22] Filed: Aug. 1, 1975

[21] Appl. No.: 601,081

Related U.S. Application Data

[63] Continuation-in-part of Ser. No. 367,239, June 5, 1973, abandoned.

[52] U.S. Cl. ............................ 23/254 E; 23/255 E; 340/237 R
[51] Int. Cl.² .................. G01N 27/16; G01N 33/22; G08B 21/00
[58] Field of Search ............ 23/254 E, 254 R, 255 E, 23/255 R, 232 E, 232 R, ; 340/237 R, 237 P; 73/27 R

[56] References Cited
UNITED STATES PATENTS

| | | | |
|---|---|---|---|
| 1,459,127 | 6/1923 | Williams et al. | 23/255 E UX |
| 2,531,592 | 11/1950 | Yant et al. | 23/232 E |
| 2,533,339 | 12/1950 | Willenborg | 23/255 E X |
| 2,821,462 | 1/1958 | McEvoy | 23/255 E |
| 2,916,358 | 12/1959 | Valentine et al | 23/254 E |
| 3,087,795 | 4/1963 | Ross | 23/255 E |
| 3,421,362 | 1/1969 | Schaeffer | 23/255 E X |
| 3,725,005 | 4/1973 | Innes | 23/255 E X |
| 3,771,960 | 11/1973 | Kim et al. | 23/254 E X |

*Primary Examiner*—Robert M. Reese
*Attorney, Agent, or Firm*—Irwin Ostroff

[57] ABSTRACT

Apparatus for detecting the presence of combustible vapors, e.g., natural gas, in the air utilizes an aluminum heat sink having a sealed reference chamber and a sensing chamber through which samples of air are continuously drawn. Separate unsupported platinum filaments that change in resistive value as a function of combustible gas which comes in contact therewith are located within the two chambers. The bottom of the sensing chamber has an input passage and an output passage with a wire mesh screen covering both passages. A solid non-porous plate having an outer perimeter slightly smaller than the inner perimeter of the sensing chamber is located above the wire mesh screen. The electrical circuitry of the apparatus includes a filament burn-out detection circuit and an unbalanced wheatstone bridge that goes through balance to the reverse unbalanced condition only if a combustible vapor comes into contact with the sensing filament.

2 Claims, 6 Drawing Figures

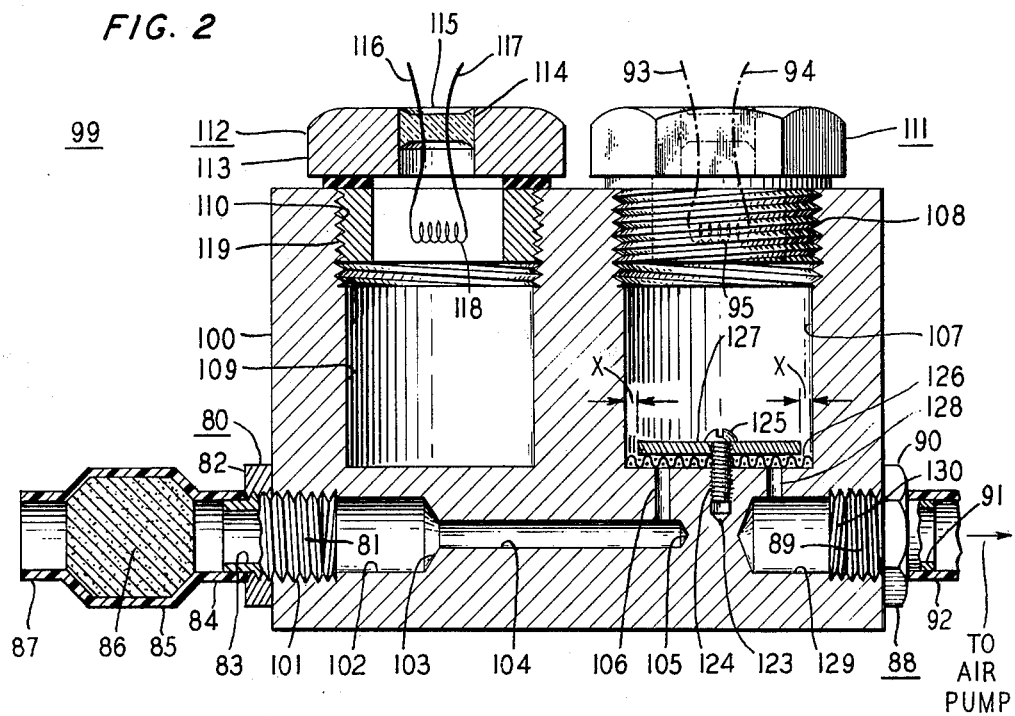
FIG. 2
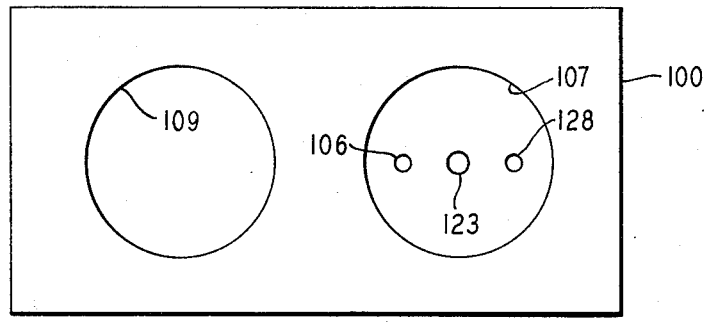
FIG. 3
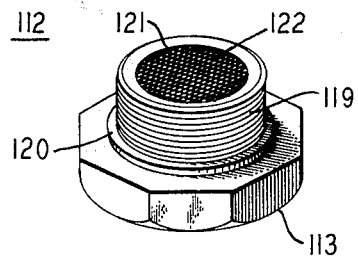
FIG. 4
FIG. 5

COMBUSTIBLE VAPOR DETECTOR

CROSS REFERENCE TO RELATED APPLICATION

This application is a continuation-in-part of application Ser. No. 367,239, filed June 5, 1973 and now abandoned.

BACKGROUND OF THE INVENTION

This invention relates to a continuously monitoring apparatus to detect combustible vapors, such as natural gas leaks in homes and industry.

A brief review of local headlines during the past few years shows an increasing incidence of natural gas explosions with resulting loss of life, personal injury and extensive property damage. Study of the incidents leads one to the conclusion that many of these incidents could have been prevented if there was early detection. Natural gas, being virtually odorless, is difficult to detect, and by the time one does smell it, as the newspaper stories indicate, explosion is seconds away. This is true even though an odor bearing compound has been added to the gas so that it may be detected more easily by smell. Many leaks occur outside the house and those inside cannot smell it since the sulphur compound gets absorbed by the soil before it enters the house. The force of a natural gas explosion is awesome, not only is one house leveled but entire blocks have been obliterated. Causes of the leaks may vary from faulty equipment within a dwelling to gas mains broken during street construction to very old corroded and leaky gas mains. Regardless of the cause, the result is inevitably the same: the loss of life and widespread property damage.

The ideal solution is equipment that never fails and an absence of accidental puncturing of gas mains. Realistically, these goals are not attainable. Detection of the leak then becomes of prime importance. Early detection of such leaks allows the occupants of a house with a leak and their neighbors to clear the area and allows time for emergency crews to shut off the supply of gas in the vicinity of the leak.

Various devices are available for detection of gas leaks. Mine Safety Appliances Co. has a carbon monoxide alarm which is primarily intended for industrial use. The device utilizes a charcoal scrubber to clear the air sample and a hopcalite bed and an inactive chemical bed to measure the parts per million (PPM) of combustable gas in the surrounding air. When the PPM of carbon monoxide (CO) reaches a predetermined level, the device gives an alarm. The same company also manufactures other detection equipment. This type of device has a high degree of thermal inertia, i.e., slow response time. The chemical bed, e.g., hopcalite, is effected by temperature cycling, moisture and poisoning. This type of device needs frequent readjustment.

Many of the prior art devices made to detect natural gas, which comprises methane, oxygen and nitrogen, are "one-shot" affairs. That is, one takes the unit to various localities, say within a plant, turns the machine on and takes a reading. All of these devices fall into the category of "detectors."

U.S. Pat. No. 2,533,339, Willenborg, describes a combustible vapor detector consisting of a metal block having a reference and a sensing chamber with a separate metallic filament located in each. The sensing chamber is an open communication with a passage through the block which allows air which normally flows through the block and may or may not contain combustible vapors to come in contact with the filament in the sensing chamber. A wire mesh screen across the bottom of the sensing chamber acts as a flame arrestor. A wheatstone bridge, which is normally in a balanced condition, is connected to both filaments. If combustible vapor comes in contact with the sensing filament the resistance thereof is changed, the bridge becomes unbalanced, and an alarm is set off. Also a fan is energized that evacuates the air surrounding the apparatus and thereby clears the area of combustible vapors. The Willenborg device has many shortcomings. The detection time is relatively poor since air samples are not forced past the sensing filament but are just allowed to normally flow through the apparatus without any bias being applied thereto. This can result in a mixture of air and combustible gas which may not be detected until an explosive mixture is formed. Another negative feature of the Willenborg apparatus is that turbulence in the air samples which reach the sensing filament can give rise to false alarms being set off. In addition, variations in the resistance of the filament for reasons other than those associated with combustible vapor can easily trigger false alarms since the wheatstone bridge is relatively easily unbalanced.

U.S. Pat. No. 3,087,795, Ross, teaches the use of an instrument which is unbalanced for a zero combustible gas concentration, but becomes balanced for a specific gas concentration. This kind of unbalanced instrument could be used with the Willenborg apparatus to help reduce false alarms.

The use of a porous diffuser element behind and completely covering the mesh wire screen of the willenborg sensing chamber would substantially eliminate most of the turbulence in samples of air which would reach the sensing filament. This would also further limit false alarms. The addition of pumping air samples past the above-modified sensing chamber would, to some extent, improve the response time. The response time would still be relatively poor because of the relatively slow process of diffusion. This problem could be attenuated if air samples were pumped solely through the wire mesh and diffuser and then forced to exit at some point in the sensing chamber after the sensing filament. This approach would limit air turbulence and produce a faster flow of samples of air past the filament. One problem with this solution is that the diffuser element would have to be relatively large to enable a sufficiently large amount of air to be pumped through the sensing chamber. The large size of the diffusion element would be difficult to achieve economically.

The flow of air over a platinum filament causes the filament to slowly age, i.e., oxidation occurs which increases the resistance of the filament. The greater the flow of air over a platinum filament the shorter the useful lifetime thereof. The resulting increase in resistance of the filament makes frequent readjustment of the apparatus necessary. Thus it is undesirable to have a large flow of air over the filament because of the shortened lifetime of the filament and the need for frequent readjustment of the apparatus.

It would be desirable to have a combustible gas detector that has a relatively fast detection time, provides continuous monitoring, is very sensitive to the presence of combustible gas or vapor, is relatively insensitive to turbulence in the air being sampled, is relatively insensitive to electric or temperature changes caused by effects other than combustible vapor or gas, is not in need of frequent readjustment, and is economically within the reach of most residential homeowners.

SUMMARY OF THE INVENTION

The present invention is a continuously monitoring high sensitivity combustible vapor detector which utilizes a heat sink having a reference chamber and a sensing chamber. The reference and sensing chambers each contain separate essentially identical filaments which vary in resistive value as a function of the amount of combustible vapor which comes into contact therewith. The reference chamber is sealed.

The sensing chamber has sidewalls and a lower section which is located below the sensing filament. The lower section has a bottom portion that has at least one entrance and one exit passage. A flame arrestor, typically a mesh wire screen, covers the bottom portion of the lower section of the sensing chamber. A solid non-porous plate is located above the flame arrestor and below the sensing filament. The outer perimeter of the plate is slightly smaller than the inner perimeter of the sidewalls of the lower section of the sensing chamber. This results in a small space between the plate and the sidewalls of the lower section of the sensing chamber. A suction pump C coupled to the exit passage of the sensing chamber.

A steady flow of air, which may or may not contain combustible gas or vapor, is pulled into the entrance passage of the sensing chamber, through the sensing chamber, and then out the exit passage by the suction pump. Most of the air entering the sensing chamber passes through the mesh wire screen and then out the exit passage. Only a small but steady portion of the air entering the sensing chamber passes through the relatively small space between the sidewalls of the sensing chamber and the solid non-porous plate and flows past the sensing filament before exiting the sensing chamber. Most of the air pulled into the sensing chamber passes through only the mesh screen. The solid non-porous plate helps insure that the small but steady flow of air which does pass the sensing filament is relatively free of turbulence. This helps insure that misreadings by the sensing filament are reduced. In addition, the life of the sensing filament is relatively long since only a small sample of the total air flow entering the sensing chamber reaches the sensing filament and thus there is little aging thereof. This makes readjustment of the apparatus much less necessary than in many prior art devices.

The reference and sensing filaments are connected together to form one leg of a wheatstone bridge. The second leg of the bridge is a potentiometer. The wiper arm of the potentiometer is one output of the bridge and the common node of the sensing and reference filaments is the other output. The wiper arm of the potentiometer is so adjusted that the wheatstone bridge is unbalanced by a predetermined amount when there is substantially no combustible gas in the sensing chamber. If combustible gases are present in the sensing chamber the resistive value of the sensing filament changes and as a result the wheatstone bridge goes through balance to the reverse unbalanced condition. Both legs of the wheatstone bridge are connected to a two input comparator amplifier.

In a preferred embodiment of the invention, the comparator amplifier normally has a negative output potential when there is essentially no combustible gas in the sensing chamber. When combustible gas or vapor exists in the sensing chamber the wheatstone bridge becomes unbalanced in the reverse direction and the output potential of the comparator amplifier changes from a negative to a positive value. The output of the comparator amplifier is coupled to a switch which closes when the comparator amplifier signal goes from a negative to a positive value. A variety of alarm systems can be coupled to the switch to give an audio or visual indication of the presence of combustible gas.

The air pump provides a relatively high rate of sampling of the air surrounding the detector and thereby helps insure that an alarm is set off before a combustible mixture can occur. The combination of the wire mesh screen and the solid non-porous plate insures against flames, provides a low air resistance path through the wire mesh, and provides a relatively high resistance path between the sidewalls of the lower section of the sensing chamber and the plate. This helps insure that only a relatively small amount of the total air entering the sensing chamber comes in contact with the sensing filament. The air is a small but steady and relatively calm stream which tends to limit false alarms. The relatively small but steady flow of air past the sensing filament helps insure a relatively long useful life of the filament and greatly reduces any need to readjust the wiper arm position of the second leg of the wheatstone bridge.

The use of a wheatstone bridge which is unbalanced when no combustible gas or vapor is present in the sensing chamber, but which becomes unbalanced in the reverse direction when gas or vapor is present, helps limit false alarms.

Another important feature of applicants' invention is a filament burn-out detection circuit that is connected to both filaments and produces an alarm signal if either or both filaments burn out or break.

These and other features and advantages of the invention will be better understood from a consideration of the following detailed description taken in conjunction with the accompanying drawings.

BRIEF DESCRIPTION OF THE DRAWING

FIGS. 2, 3, 4, and 5 illustrate various views of the mechanical structures in accordance with this invention which can be utilized with the circuitry of FIG. 1 or FIG. 6.

DETAILED DESCRIPTION

Figure 1:
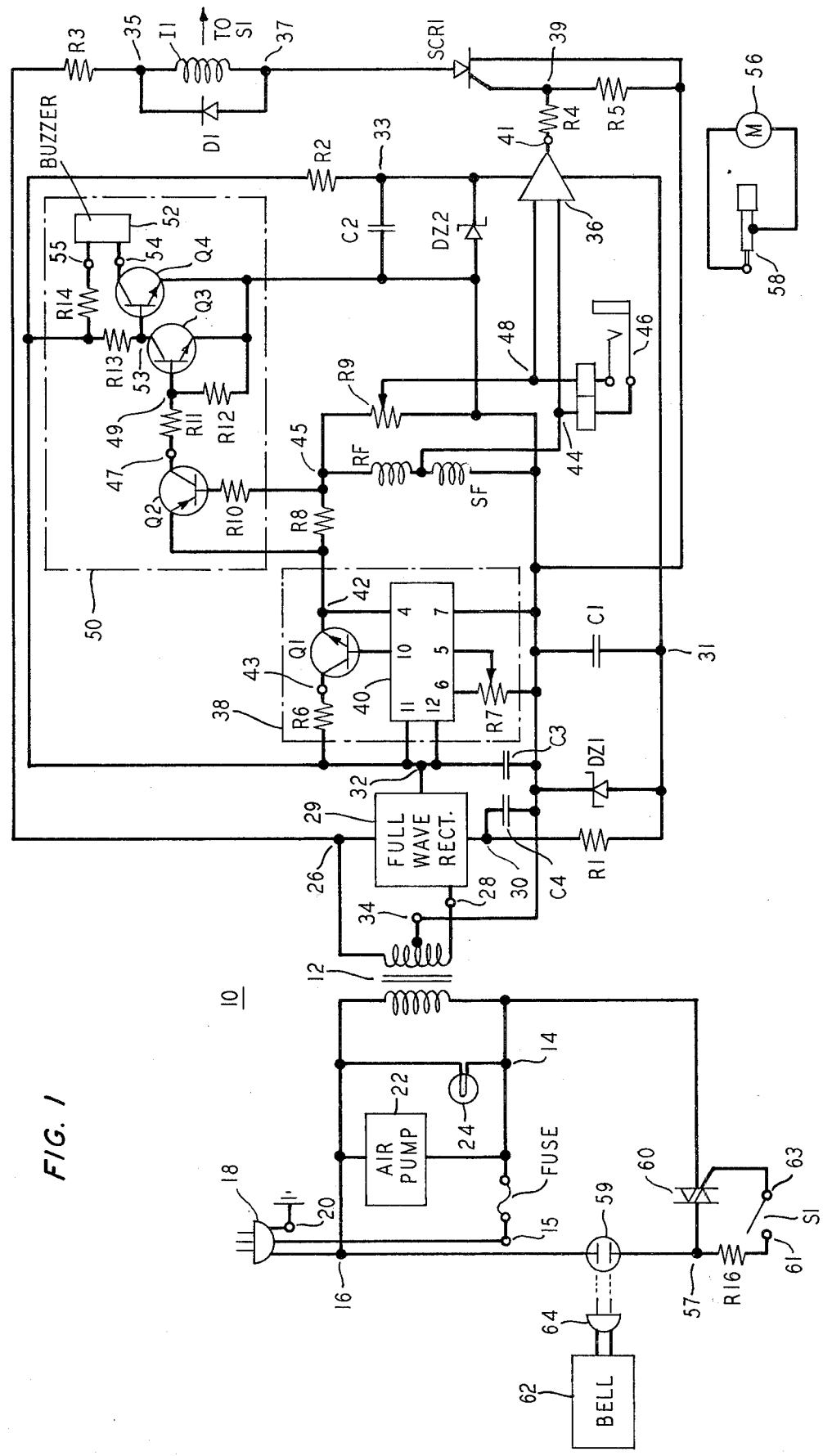
FIG. 1 illustrates in block and electrical schematic form an embodiment of a combustible vapor detector in accordance with this invention.

Referring now to FIGS. 1, 2, 3, 4, and 5, there is illustrated a combustible vapor detector system 10. FIG. 1 illustrates the basic electrical structures of system 10 and FIGS. 2, 3, 4, and 5 illustrate the basic physical structures of system 10.

System 10 has been designed to operate from household ac voltage. A step down transformer 12 has the primary side coupled to terminals 14 and 16. Terminal 14 is connected to terminal 15 through a fuse. Terminals 15 and 16 are coupled to two of the three pins of electrical plug 18. The third pin of plug 18 (terminal 20) is connected to ground potential. An air pump 22 and a light bulb 24 are both connected between terminals 14 and 16. The secondary side of transformer 12 is connected to terminals 26 and 28. A full wave rectifier 29 is coupled to terminals 26, 28, 30 and 32. A center tap on the secondary side of transformer 12 is coupled to terminal 34. Terminals 26 and 28 provide an ac voltage source which is lower in amplitude than that applied to terminals 14 and 16. Terminal 32 provides a positive dc potential and terminal 30 provides a negative dc potential. Terminal 34 provides a common potential which is electrically midway between the positive and negative potentials appearing at terminals 32 and 30.

Terminal 30 is connected to one terminal of resistor R1 and one terminal of electrolytic capacitor C4. The second terminal of C4 is connected to terminal 34. The second terminal of R1, terminal 31, is connected to the first terminal of an electrolytic capacitor C1, the anode of a zener diode DZ1, and to a two input comparator amplifier 36. The cathode of DZ1 and the second terminal of C1 are both connected to terminal 34. Terminal 32 is connected to one terminal of a resistor R2 which has the second terminal (terminal 33) connected to one terminal of an electrolytic capacitor C2, the cathode of a zener diode DZ2 and comparator amplifier 36. The anodoe of DZ2 and the second terminal of C2 are both connected to terminal 34.

Terminal 26 is coupled to one terminal of a resistor R3. The second terminal of R3, terminal 35, is connected to a first terminal of an inductor coil I1 and the cathode of a diode D1. The inductor coil I1 is wound around a switch S1 having terminals 61 and 63 so as to form a relay. When current flows through I1, terminals 61 and 63 are shorted together. The anode of D1 and the second terminal of I1 are both coupled to terminal 37, which is coupled to the anode of a silicon controlled rectifier SCR1. The gate terminal of SCR1 is coupled to the junction node of resistors R4 and R5 (terminal 39). A second terminal of R4 is connected to the output of comparator amplifier 36 (terminal 41). The second terminal of R5 and the cathode of SCR1 are both coupled to terminal 34.

Enclosed within dashed line rectangle 38 is a dc regulator circuit which comprises a commercially available integrated circuit 40 manufactured by Motorola Corporation having the number MC1723CL, a resistor R6, and N-P-N junction transistor Q1 and a potentiometer R7. Pins 5 and 6 of 40 are connected to the wiper arm of R7 and one terminal of R7, respectively. The second terminal of R7 and pin 7 are both connected to terminal 34. Pins 11 and 12 of 40, the first terminal of R6, and the first terminal of an electrolytic capacitor C3, are all connected to terminal 32. The second terminal of C3 is connected to terminal 34.

The collector and base of Q1 are coupled to the second terminal of R6 (terminal 43) and pin 10 of 40, respectively. The emitter of Q1, pin 4 of 40, and a first terminal of a resistor R8 are all coupled to terminal 42. The second terminal of R8 (terminal 45) is coupled to the series combination of a reference filament RF and a sensing filament SF and to a first terminal of a potentiometer R9. The common node (terminal 44) of RF and SF is connected to one input of comparator amplifier 36 and to one terminal of a meter jack 46. The second terminal of SF is connected to terminal 34. R9 has a wiper arm connected to terminal 48 which is connected to the second input of comparator amplifier 36 and to the second terminal of meter jack 46. The second terminal of R9 is connected to terminal 34.

Enclosed within dashed line rectangle 50 is a filament burn-out detector circuit which comprises a P-N-P junction transistor Q2, N-P-N junction transistors Q3 and Q4, resistors R10, R11, R12, R13 and R14, and a buzzer 52. The emitter of Q2 is coupled to terminal 42. One terminal of R10 is coupled to terminal 45 and the other terminal is connected to the base of Q2. The collector of Q2 is coupled to terminal 47 of R11. Terminal 49 of R11 is connected to the base of Q3 and one terminal of R12. The other terminal of R12 and the emitters of Q3 and Q4 are coupled together to terminal 34. The collector of Q3 is coupled to the base of Q4 and terminal 53 of R13. The second terminal of R13 is coupled to a first terminal of R14 and to terminal 32. Terminal 55 of R14 is coupled through buzzer 52 to the collector of Q4 (terminal 54).

A null balance voltage meter 56 is connected to a plug 58, which is adapted to be plugged into meter jack 46.

Terminal 14 is coupled to one output terminal of a triac 60. Terminal 16 is connected to one terminal of an electrical outlet 59. A terminal 57 of electrical outlet 59 is connected to the second output terminal of 60 and to a first terminal of a resistor R16. The second terminal of R16 is connected to terminal 61 of relay switch S1. Terminal 63 serves as the second terminal of S1 and is coupled to the gate of 60.

An alarm bell circuit 62 is connected to a plug 64 which is adapted to fit into socket 59.

Ac power (typically household voltage) supplied to electrical plug 18 is lowered in potential by transformer 12 and then converted to dc by full wave rectifier 29. Positive dc voltage appearing at terminal 32 is filtered by C3, and negative dc voltage appearing at terminal 30 is filtered by C4. DZ2 and DZ1 are operated in avalanche breakdown and serve to regulate the positive and negative potentials appearing at terminals 33 and 31, respectively. R1 and R2 both serve to limit current dissipation. The dc regulator within dashed line rectangle 38 produces a well regulated dc voltage at terminal 42. Terminal 42 appears as an essentially ideal voltage source. Current flows from terminal 42 through resistor R8 and into the series combination of RF and SF and also through R9, which is in parallel with RF and SF. RF and SF form one leg of a wheatstone bridge and R9 forms the other leg.

RF is physically contained within a reference chamber 109 of a metallic heat sink element 100 that is illustrated in FIG. 2. SF is physically located within a sensing chamber 107 located within 100 of FIG. 2. With no combustible gas in the sensing chamber the wiper arm of R9 is set such that the voltage that appears at terminal 48 is more positive than the potential appearing at terminal 44. Comparator amplifier 36, which is used as a voltage comparator, detects the voltage imbalance between the two legs of the wheatstone bridge.

RF and SF are both typically platinum metallic filaments which vary in resistance as a function of combustible gas which comes into contact therewith. As will become clear from the description of FIG. 2, combustible gas can only come in contact with the sensing filament. Normally, when there is no combustible gas or vapor present, the potential of terminal 44 is less than that of terminal 48. This results in the output of 36 (terminal 41) being negative. If combustible gas comes in contact with SF, the resistance thereof increases and consequently the potential of terminal 44 rises and the wheatstone bridge becomes imbalanced in the reverse direction. The output of 36 at terminal 41 changes from a negative to a positive potential. This change in voltage is coupled through R4 to the gate (terminal 39) of SCR1.

Normally, the gate potential of SCR1 is not sufficiently positive to allow conduction therethrough. However, when the output of 36 goes positive in response to combustible vapors coming in contact with SF, SCR1 is positively biased such that conduction occurs therethrough. This conduction flows through I1. The conduction through I1 causes a magnetic field to be set up which causes S1 to close and therefore for terminal 61 to be connected to terminal 63. Triac 60, which had been turned off since S1 was open is now turned on. 60 acts as an essentially short circuit and the household ac voltage applied across terminals 14 and 16 is connected across the terminals 16 and 57 of outlet 59. This energizes alarm bell 62 and thus an audio signal is created which indicates that combustible gas has come in contact with the sensing filament. When combustible gas ceases to contact SF the output of 36 returns to a negative value and SCR1 is turned off. This cuts off the current flow through I1 which consequently causes S1 to open and thereby turns off 60. Thus, outlet 59 no longer has an ac voltage potential across terminals 16 and 57 and alarm bell 62 ceases sending out an audio alarm signal.

The burn-out detector circuit enclosed within dashed line rectangle 50 operates as follows: Normally current flows through RF and SF and R9. This current causes a voltage drop across R8 that is sufficient such that the emitter-base potential of Q2 is sufficiently positive to allow conduction through Q2. This conduction causes the potential of the emitter-base junction of Q3 to be sufficiently positive to enable Q3 to operate in a saturation mode. This in turn causes the voltage of the collector Q3 to be sufficiently low such that the emitter-base junction of Q4 has insufficient forward bias to allow conduction therethrough. The buzzer 52 coupled to the collector Q4, (terminal 54) thus receives no current and consequently no alarm is signaled. If either of the two filaments RF or SF burns out or breaks, the current level through R8 is significantly reduced and the emitter-base junction potential of Q2 is reduced such that conduction through Q2 ceases. This cuts off the supply of base current to Q3 which then ceases to conduct. The potential of terminal 53 rises such that the emitter-base junction of Q4 is sufficiently forward biased to allow conduction through Q4. This conduction, which occurs through the series combination of R14 and buzzer 52, gives rise to the buzzer 52 being set off which indicates that one of the two filaments has burned out.

D1, which is connected across the terminals 35 and 37, serves to limit the possible voltage excursion which exists during the collapsing of the magnetic field set up in I1 when current ceases to flow therethrough. R3 serves to limit the current that flows through SCR1.

Referring now to FIGS. 2 through 5, there is illustrated a structure 99 which comprises a heat sink 100 which contains a threaded bore 101 which merges into a smooth bore 102. The end of bore 102 is counter sunk at 103 and is in communication with a narrow bore 104. Bore 104 terminates at 105 and is in communication with inlet bore 106. Inlet bore 106 is in communication with a bottom portion of a lower section of a sensing chamber 107 which is threaded at a top portion 108 thereof. The base of chamber 107 is bored and tapped as at 123 to receive a screw 124 having a head 125. A mesh wire screen 126 covers the bottom portion of the lower section of sensing chamber 107. Between head 125 and mesh wire screen 126 is a solid non-porous plate element 127 having an outer perimeter which is slightly less than the inner perimeter of the sidewalls of the lower portion of sensing chamber 107. The distance X is typically on the order of a few thousands of an inch. The meshed wire screen 126 acts as a flame arrestor. The plate element 127 acts as an air sampler and air calmer.

Adapter element 80 comprises a threaded portion 81, a nut portion 82, and a tube portion 83. The threaded portion 81 is adapted to be engaged by a wrench to insert element 80 into the threaded bore 101. A plastic tube 84 having an inner diameter which is slightly larger than the outer diameter of 83 is inserted over 83. Tube 84 has a section 85 which contains a charcoal filter element 86 and an open section 87 which is in open communication with the air which surrounds system 10 of FIG. 1 or system 10' of FIG. 6.

An adapter element 88 comprises a threaded portion 89, a nut portion 90, and a tube portion 91. Threaded portion 89 is adapted to be engaged by a wrench to insert element 88 into threaded bore 180. A plastic tube 92 having an inner diameter which is slightly larger than the outer diameter of 91 is inserted over 91. Tube 92 is coupled to air pump 22 of FIG. 1 or air pump 22' of FIG. 6.

An exit outlet in the bottom portion of the lower section of sensing chamber 107 is in communication with bore 128 which is in communication with bore 129. Bore 129 is threaded at one end.

An essentially sealed reference chamber 109 having a top threaded section 119 and being essentially the same physical size as sensing chamber 107 exists in 100. Threaded into the top of each of chambers 107 and 109 of 100 are commercially available sensing elements 111 and 112. These elements are essentially identical so only one will be described.

Element 112 consists of a nut portion 113, which is adapted to be engaged by a wrench to insert the element into the block 100, and a threaded portion 119 adapted to engage threads 110. There is a bore 114 through the element 112 and a glass or ceramic seal 115 in the top portion thereof which encases filament wires 116 and 117. These wires are joined by coiled platinum wire portions 118, which is illustrated as the reference filament. The bottom portion of element 112 has a sealing gasket 120 (see FIG. 4) and a stainless steel screen 122 fitted into an aperture 121 in the bottom thereof.

Figure 6:
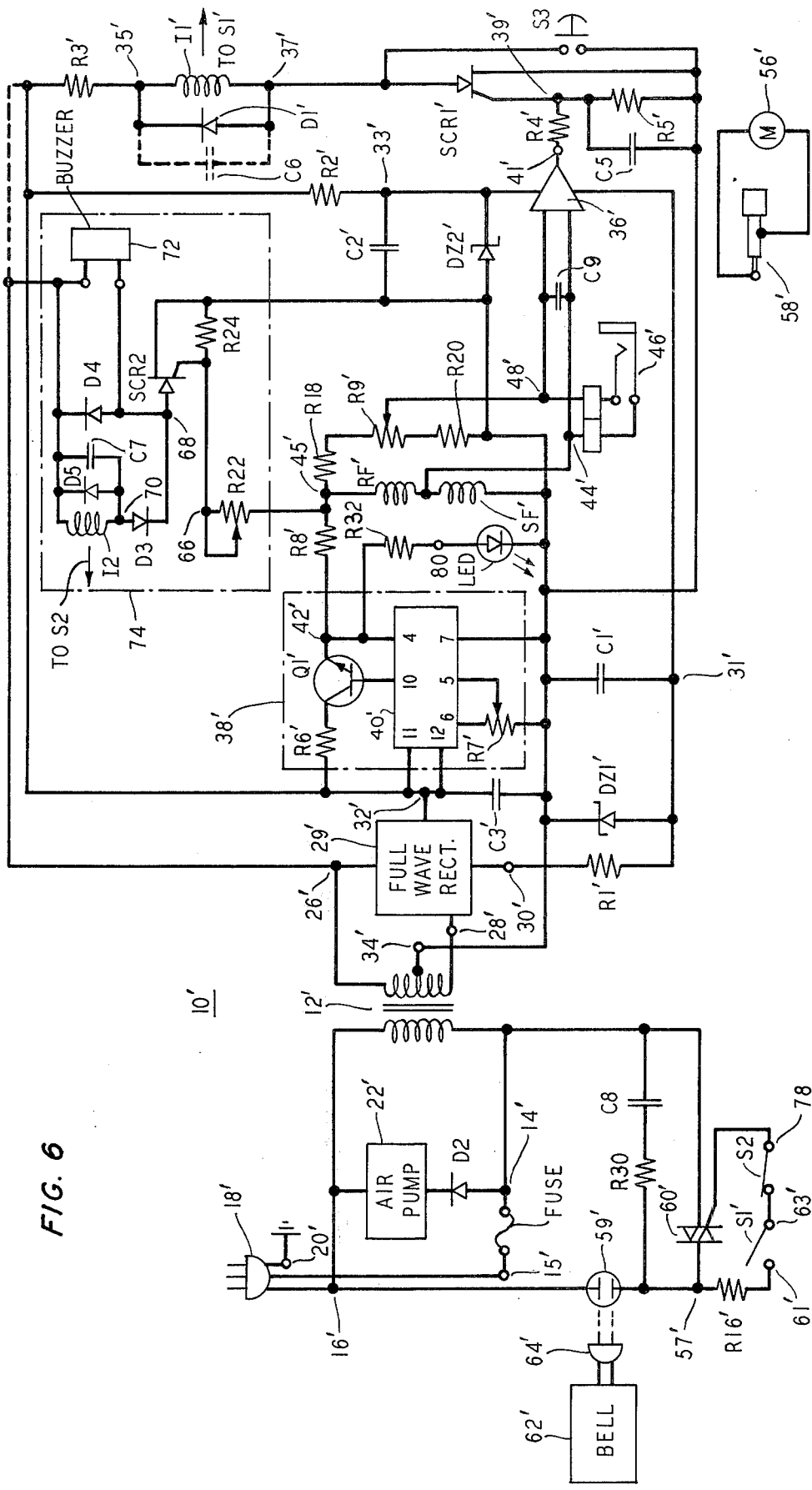
FIG. 6 illustrates in block and electrical schematic form a preferred embodiment of a combustible vapor detector in accordance with this invention.

The air pump 22 of FIG. 1 or air pump 22' of FIG. 6 pulls air through 87 into the inlet passage to the bottom portion of the sensing chamber 107. Most of the air pulled into the sensing chamber passes through mesh wire screen 126 and out the exit passage and then through bores 128, 129, and tube 91 to the air pump 22 of FIG. 1 or air pump 22' of FIG. 6. The solid non-porous plate element 127 allows only a small but steady and calm flow of air to pass between element 127 and the sidewalls of the lower section of the sensing chamber 107. This relatively small but steady and calm flow of air, which may or may not contain combustible gases or vapors, passes the sensing filament and then passes again between the sidewalls of the lower section of the sensing chamber and the plate 127 and then passes through the mesh wire screen 126 and out the exit passage of 107 and back to the air pump 22 or air pump 22', of FIGS. 1 and 6, respectively. The small but steady flow of air that does pass the sensing filament is relatively calm and free of turbulence because of the construction, physical size, and location of element 127. This is significant because turbulence in air samples which reach the sensing filament can cause erroneous readings which give rise to false alarms being set off.

The air pump provides a relatively high rate of sampling of the air surrounding the detector and thereby helps insure that an alarm is set off before a combustible mixture can occur. The combination of the wire mesh screen and the solid non-porous plate insures against flames, provides a low air resistance path through the wire mesh, and provides a relatively high resistance path between the sidewalls of the lower section of the sensing chamber and the plate. This helps insure that only a relatively small amount of the total air entering the sensing chamber comes in contact with the sensing filament. The stream of air which reaches the filament is relatively small, steady and calm. This tends to limit false alarms. The relatively small but steady flow of air past the sensing filament helps insure a relatively long useful life of the filament and greatly reduces any need to readjust the position of the wiper arm of the second leg of the wheatstone bridge.

The use of a wheatstone bridge which is unbalanced when no combustible gas or vapor is present in the sensing chamber, but which becomes unbalanced in the reverse direction when gas or vapor is present, helps limit false alarms.

A wheatstone bridge which is balanced when no combustible gas is present can easily cause a false alarm to be set off due to changes in the resistance of one or the other legs.

Block 100 is typically made of aluminum and acts as a heat sink. The mass of block 100 stays at basically the ambient temperature and thus there is no need to heat the block. The filament size or mass of the reference and sensing filaments is extremely small in comparison to the block size. Generally speaking, the larger the mass ratio of block to filaments the better.

Combustible vapor detector system 10 is very sensitive and can detect 0.05 percent of natural gas in the air. Typically 2 stand. cu. ft. per hour are drawn through the sensing chamber by air pump 22.

Referring now to FIGS. 2, 3, 4, 5, and 6, there is illustrated a preferred embodiment of a combustible vapor detector system 10'. System 10' is very similar to system 10 of FIG. 1 and both utilize the physical structures of FIGS. 2, 3, 4, and 5. The components of system 10' that are similar or identical to those of system 10 and perform essentially the same functions are illustrated with the same reference markings with a prime added thereafter. For example, full wave rectifier 29 of FIG. 1 is essentially identical to full wave rectifier 29' of FIG. 6.

Enclosed within a dashed line rectangle 74 is a filament burn-out detector circuit which comprises a silicon controlled rectifier SCR2, diodes D3, D4, and D5, an ac buzzer 72, an inductor I2, a capacitor C7, a resistor R24, and a potentiometer R22 which is connected as a resistor. This filament burn-out detector circuit performs essentially the same function as the burn-out detector circuit of FIG. 1 (illustrated within dashed line rectangle 50) and has one other function which will be discussed later.

One terminal of buzzer 72, the cathodes of D4 and D5, and one terminal of I2 and C7 are all coupled to terminal 26'. A second terminal of 72, the anode of D4, the anode of SCR2, and the cathode of D3 are all coupled to terminal 68. A second terminal of I2, a second terminal of C7, the anode of D5, and the anode of D3 are all coupled to terminal 70. A first terminal of R24, the control gate of SCR2, and the wiper arm and one terminal of R22 are all coupled to terminal 66. A second terminal of R22 is coupled to terminal 45'. Inductor I2 is part of a reed relay switch S2 which is not completely illustrated within dashed line rectangle 74. S2 couples terminals 63' and 78 together and thus connects the control gate of a t triac 60' to terminal 63' of a reed relay switch S1'. The cathode of SCR2 and the second terminal of R24 are both coupled to terminal 34'. S2 is normally closed and S1' is normally open.

If one of the filaments RF' or SF' burns out or breaks, conduction is created through I2 which causes S2 to open and thus disconnects terminals 63' and 78. This effectively prevents current flow through thus insures that alarm bell 62' will not be energized and thus will not signal an alarm. Current also passes through buzzer 72 and sets off an audio signal which indicates that one of the filaments has burned out. Without the inclusion of I2 and S2 it is possible that alarm bell 62' could be activated at the same time that buzzer 72 is activated. This would make it difficult to determine which alarm is sounding and what the problem is. This problem could be solved by replacing buzzer 72 with a lamp and thus eliminating the need for I2 and S2. In some instances this may be acceptable, however, in other instances an audio signal is desirable.

The burn-out detector circuit contained within dashed line rectangle 74 operates as follows: Normally current flows past R8' and into the two legs of the wheatstone bridge which comprises SF' and RS', and R9', and resistors R18 and R20. This current flow through R8' results in terminal 45' reaching a potential which is not sufficiently positive to allow terminal 66 to reach a potential which will enable SCR2 to conduct. As long as SF' and RS' are conducting no current flow exists through I2, buzzer 72, or SCR2. S2 remains closed at this time. If either RF' or SF' burns out or breaks, the current level flowing through R8' is significantly reduced and the potential of terminal 45' is increased such that the potential of the terminal 66 (the control gate of SCR2) increases to a level at which SCR2 is turned on and current flows through I2, 72, and SCR2 to terminal 34'. This condition sets off buzzer 72 and causes S2 to open and thus disconnect terminals 63' and 78. This disables 60' and thus prevents 59' from being activated at this time. Thus 62' cannot give an audible alarm.

With the second terminal of R3' coupled to terminal 32' (a dc voltage source), once dc current flows through R3',I1', and SCR1' it will continue even if the potential of the control gate (terminal 39') of SCR1' is lowered in potential to a potential which is not sufficient to start conduction through SCR1'. This is because one characteristic of an SCR is that it continues to conduct dc current once established even after the voltage bias applied to the control gate terminal 39' is removed. This condition causes S1' to stay closed and thus terminal 61' is coupled to terminals 63', 78, and the control gate terminal of triac 60'. This energizes bell 62' which then gives an audio alarm. In some applications it is desirable that if any combustible gas is sensed that an alarm be set off and that the alarm continue even if the combustible gas which caused the alarm is no longer present. With the second terminal of R3' connected to terminal 32, as is illustrated, this situation is achieved. Switch S3, which is across terminals 37' and 34', is normally open. When switch S3 is pushed in and terminal 37' is shorted to terminal 34' conduction through SCR1' is halted. When switch S3 is released it automatically opens. No current flow exists now through SCR1' unless the proper positive potential is once again applied to control gate terminal 37'. This positive potential is only set up if combustible gas is again detected.

If the first terminal of R3' is coupled to terminal 26' (an ac voltage source), as is illustrated by the dashed line, and the solid line connection shown to terminal 32' is disconnected, then the current that will flow through I1' and SCR1' is ac rather than dc. With R3' so connected, a capacitor C6, illustrated in dashed line, is connected across terminals 35' and 37'. S3 is not needed for this configuration. When combustible gas is sensed terminal 39' goes from a negative to a positive potential and thus causes a flow of current through I1' and SCR1'. This flow of current causes S1' to close and thus energizes 62' which provides an audio alarm. If the combustible gas which had been sensed ceases to contact the sensing filament, terminal 39' returns to a negative potential and conduction through I1' and SCR1' ceases. Thus, S1' opens and 62' ceases to emit an audio alarm. In many instances this type of configuration is desirable since it is only necessary to know if combustible vapor continues in a given area around system 10' and not whether at some one instance in time there was combustible vapor or gas present.

A resistor R32 is coupled between terminal 42' and a terminal 80 that is coupled to the anode of a light emitting diode, LED. The cathode of the LED is coupled to terminal 34'. The LED emits light if the transformer 12', full wave rectifier 36', and the dc regulator contained within dashed line rectangle 38', are operating properly.

A capacitor C9 is coupled between terminals 44', and 48'. This capacitor helps equalize noise and other spurious ac signals and thus helps insure against the setting off of false alarms.

A capacitor C5 is coupled between terminals 39' and 34'. C5 modifies the shape of the voltage waveform of terminal 39' and thus limits ac transients which helps limit false alarms.

The RC series combination of a resistor R30 and a capacitor C8 across terminals 57' and 14' serves to limit voltage transients created by the collapsing magnetic field of 62'.

Diode D2, which is illustrated with the anode coupled to 14' and the cathode coupled to air pump 22' serves as a half wave rectifier.

D1 and D5 both serve to limit the possible voltage excursion which exits during the collapsing of the magnetic fields set up in I1' and I2, respectively.

In an embodiment of the invention which has been fabricated and tested, the components and values thereof are as follows: (All resistor values in ohms and all capacitor value are in microfarads)

| | |
|---|---|
| R1' = 220 | C1' = 450 |
| R2' = 220 | C2' = 450 |
| R3' = 47, 10[(1)] | C3' = 2200 |
| R4' = 3300 | |
| R5' = 1000 | C5 = .1 |
| R6' = 10 | C6 = 100 |
| | C7 = 100 |
| R8' = 1 | C8 = .1 |
| R9' = 10 | C9 = 1 |
| R17' = 2700 | DZ1 = 1N4739A |
| R18 = 20 | DZ2 = 1N4739A |
| R20 = 20 | D2 = 1N2483 |
| R22 = 1000 | D3 = 1N914 |
| R24 = 470 | D4 = 1N914 |
| R30 = 2700 | SCR1' = TIC45 |
| R32 = 47 | SCR2 = TIC45 |

[(1)]When R3 is connected to 32' the ohmic value is 10.

Triac 60' = T2313B(RCA)
The Magnecraft - W171D1P-9 includes I1', S1' and D1' in one unit and I2, S2, and D5 in a second unit.

When R3 is connected to 26' the ohmic value is 47.
40' = MC17223CL
Q1' = 2N305
36' = 741
Differential Amplifier System 10' can detect 0.05 percent of natural gas in air and typically samples 2 stand. cu. ft. per hour of surrounding air. When manufactured in volume it is believed the price per unit will be within the range of most residential homeowners. Essentially all of the advantages denoted for System 10 of FIG. 1 are equally applicable to System 10' of FIG. 6. The high sensitivity, relatively fast detection time, relatively high reliability, infrequent need for readjustment, and relatively low estimated cost, make the present invention a viable candidate for wide spread use to protect homes and industry from the calamity of gas explosions. The combination of the air pump, mesh screen, solid plate, and an unbalanced wheatstone bridge which becomes unbalanced in the reverse direction when gas is detected, results in a combustible gas detector which is clearly superior to all those presently available and known of to applicants.

The embodiments described herein are intended to be illustrative of the general embodiments of the invention. Various modifications are possible consistent with the spirit of the invention. For example, the output of the comparator amplifier could be directly coupled to an alarm generator which could emit a visual or audio alarm signal. Still further, a variety of different ac to dc convertors or voltage regulators could be used. Still further, the output of the comparator amplifier could be connected to a control device which turns off the flow of combustible gas (i.e., natural gas).

What is claimed is:

1. Apparatus for detecting combustible vapors comprising:
   heat sink means, the structure of the heat sink means defining a reference chamber and a sensing chamber;
   the sensing chamber being characterized by a lower section which has a bottom portion and sidewalls which have a preselected interior perimeter;
   the reference chamber being essentially sealed;
   at least one entrance passage and one exit passage being physically separated one from the other and both being located in the bottom portion of the lower section of the sensing chamber;

first and second essentially identical filament means, both of the filament means being adapted to vary in resistive value as a function of the amount of combustible vapor present in air which comes into contact with the filament means;

first circuit means coupled to the first and second filament means, the first circuit means being adapted to generate a first alarm signal if either filament means breaks or burns out;

the first and second filament means being located essentially within the sensing chamber and reference chamber, respectively;

second circuit means comprising a wheatstone bridge circuit having first and second resistive circuit legs, the first leg comprising the first and second filament means, the resistive value of the first and second legs being selected such that when there are substantially no combustible vapors in the sensing and reference chambers the wheatstone bridge is unbalanced, however, if there is a significant amount of combustible vapor in the sensing chamber and substantially none in the reference chamber, the wheatstone bridge goes through balance to an unbalanced condition in the reverse direction;

alarm circuit means being coupled to the wheatstone bridge, the alarm circuit means being adapted to generate a second alarm signal if and only if the wheatstone bridge goes through balance to an unbalanced condition in the reverse direction;

first conduit means in open communication with the entrance passage of the bottom portion of the lower section of the sensing chamber;

second conduit means in open communication with the exit passage of the bottom portion of the lower section of the sensing chamber;

air pumping means in communication with the second conduit means, the air pumping means being adapted to continuously draw air, which may or may not contain combustible gases or vapors, into the first conduit means, through the sensing chamber, and out of the second conduit means;

air sampling and calming means and flame arresting means, both the air sampling and calming means and the flame arresting means being located in the lower section of the sensing chamber;

the flame arresting means being physically located below the air sampling and calming means and being located so as to overlap the entrance and exit passages in the sensing chamber;

the air sampling and calming means being an essentially solid non-porous member, the outer perimeter of the member being slightly smaller than the interior perimeter of the sidewalls of the lower section of the sensing chamber such that a relatively small space exists between the sidewalls of the lower section of the sensing chamber and the air sampling and calming means; and the air sampling and calming means having a much higher resistance to the flow of air therepast than the flame arresting means such that only a relatively small amount of the total air continuously drawn into the sensing chamber by the air pumping means continuously passes above the air sampling and calming means and enters the portion of the sensing chamber which contains the sensing filament.

2. The apparatus of claim 1 wherein:

the sidewalls of the lower section of the sensing chamber are cylindrical and the solid non-porous member is plate-like;

the heat sink means is a metallic block; and the alarm circuit means comprises a two input comparator amplifier having an output terminal that is coupled to the control terminal of a switch that is coupled to an alarm generator element.

* * * * *